US010603439B2

(12) United States Patent
Strader

(10) Patent No.: US 10,603,439 B2
(45) Date of Patent: Mar. 31, 2020

(54) SEALED SELF-ACTIVATING INJECTION DEVICE FOR DELIVERY OF MEDICINE FROM A PREFILLED CARTRIDGE OR VIAL

(71) Applicant: KPR U.S., LLC, Mansfield, MA (US)

(72) Inventor: David L. Strader, Debary, FL (US)

(73) Assignee: KPR U.S., LLC, Mansfield, MA (US)

( * ) Notice: Subject to any disclaimer, the term of this patent is extended or adjusted under 35 U.S.C. 154(b) by 999 days.

(21) Appl. No.: 14/481,377

(22) Filed: Sep. 9, 2014

(65) Prior Publication Data

US 2015/0073353 A1 Mar. 12, 2015

Related U.S. Application Data

(60) Provisional application No. 61/875,274, filed on Sep. 9, 2013.

(51) Int. Cl.
*A61M 5/24* (2006.01)
*A61L 2/08* (2006.01)
(Continued)

(52) U.S. Cl.
CPC ........... *A61M 5/2466* (2013.01); *A61L 2/081* (2013.01); *A61L 2/10* (2013.01); *A61M 5/24* (2013.01);
(Continued)

(58) Field of Classification Search
CPC .......... A61M 5/2466; A61M 2005/247; A61M 2005/2407; A61M 2005/2474;
(Continued)

(56) References Cited

U.S. PATENT DOCUMENTS 3,783,997 A 1/1974 Brown
3,784,997 A * 1/1974 Beck ....................... A47L 23/02
15/31
(Continued)

FOREIGN PATENT DOCUMENTS

EP 0740942 A1 11/1996
EP 2540329 A1 1/2013
(Continued)

OTHER PUBLICATIONS

Office Action dated Nov. 2, 2016 in related Canadian Application No. 2923416, 3 pages.
(Continued)

*Primary Examiner* — Emily L Schmidt
(74) *Attorney, Agent, or Firm* — Arent Fox LLP

(57) ABSTRACT

The disclosed embodiment relates to an injection device that is a single patient use, disposable device containing a needle and a cartridge containing a drug or pharmaceutical product. The device is initially provided in a pre-armed configuration wherein the needle sheath maintains cantilever locking tabs on the housing in a position to the maintain the needle in a position separated from the septum of a cartridge. To arm the device, the practitioner removes the needle sheath and pushes down the plunger assembly. The cantilever locking tabs flex outwardly thereby allowing the cartridge-to-housing interface and the cartridge to move forward whereby the butt end of the needle punctures the septum of the cartridge. Additionally, the cantilever locking tabs form a stop configuration with the housing of the device. The disclosed embodiment is particularly adaptable to dental anesthetic applications, as well as other medical and veterinary applications.

31 Claims, 19 Drawing Sheets

(51) Int. Cl.
*A61L 2/10* (2006.01)
*A61M 5/32* (2006.01)
*A61M 5/20* (2006.01)
*A61M 5/315* (2006.01)

(52) U.S. Cl.
CPC ....... *A61M 5/3202* (2013.01); *A61M 5/31578* (2013.01); *A61M 2005/2073* (2013.01); *A61M 2005/247* (2013.01); *Y10T 29/4984* (2015.01)

(58) Field of Classification Search
CPC .... A61M 5/31571; A61M 2005/31508; A61M 5/31505; A61M 5/31501; A61M 5/24; A61M 2005/2492; A61J 1/1406; A61J 1/062
See application file for complete search history.

(56) References Cited

U.S. PATENT DOCUMENTS

| | | | | |
|---|---|---|---|---|
| 3,895,633 | A | * | 7/1975 | Bartner ................. A61M 5/178 604/192 |
| 4,808,169 | A | * | 2/1989 | Haber ..................... A61M 5/24 604/110 |
| 4,834,717 | A | * | 5/1989 | Haber ..................... A61M 5/24 604/193 |
| 5,478,321 | A | | 12/1995 | Kimber |
| 5,695,477 | A | | 12/1997 | Sfikas |
| 5,931,817 | A | | 8/1999 | Nguyen et al. |
| 5,997,513 | A | | 12/1999 | Smith et al. |
| D608,886 | S | | 1/2010 | Rueckert et al. |
| 8,034,034 | B2 | | 10/2011 | Hess et al. |
| 8,152,763 | B2 | | 4/2012 | Epperson |
| 8,852,158 | B1 | | 10/2014 | Schaffer |
| 2001/0053886 | A1 | | 12/2001 | Caizza |
| 2007/0060897 | A1 | | 3/2007 | Wang |
| 2007/0078408 | A1 | | 4/2007 | Wang |
| 2007/0265579 | A1 | | 11/2007 | Kleyman et al. |
| 2008/0051729 | A1 | | 2/2008 | Cheng |
| 2009/0137966 | A1 | | 5/2009 | Rueckert et al. |
| 2011/0092917 | A1 | | 4/2011 | Wei et al. |
| 2013/0018311 | A1 | | 1/2013 | Denning et al. |
| 2016/0158101 | A1 | | 6/2016 | Latiolais |

FOREIGN PATENT DOCUMENTS

| | | |
|---|---|---|
| WO | 89/02760 A1 | 4/1989 |
| WO | 2007/008257 A2 | 1/2007 |
| WO | 2012/000554 A1 | 1/2012 |
| WO | 2013/063707 A1 | 5/2013 |
| WO | 2013/134246 A1 | 9/2013 |

OTHER PUBLICATIONS

International Preliminary Report on Patentability issed in International Application No. PCT/US2014/054765, dated Jun. 5, 2015.
International Preliminary Report on Patentability issed in International Application No. PCT/US2014/054775, dated Dec. 23, 2015.
International Search Report and Written Opinion issed in International Application No. PCT/US2014/054765, dated Nov. 24, 2014.
International Search Report and Written Opinion issed in International Application No. PCT/US2014/054775, dated Nov. 24, 2014.
Written Opinion of the International Preliminary Examining Authority issued in International Application No. PCT/US2014/054765, dated Mar. 12, 2015.
Written Opinion of the International Preliminary Examining Authority issued in International Application No. PCT/US2014/054775, dated Mar. 20, 2015.
Examination Report for European Patent Application No. 14766872.7, dated Aug. 21, 2018, 7 pages.
Office Action dated Oct. 25, 2016 in related Canadian Application No. 2923171, 3 pages.
Office Action dated Oct. 3, 2017 in related U.S. Appl. No. 14/481,303, 13 pages.

* cited by examiner

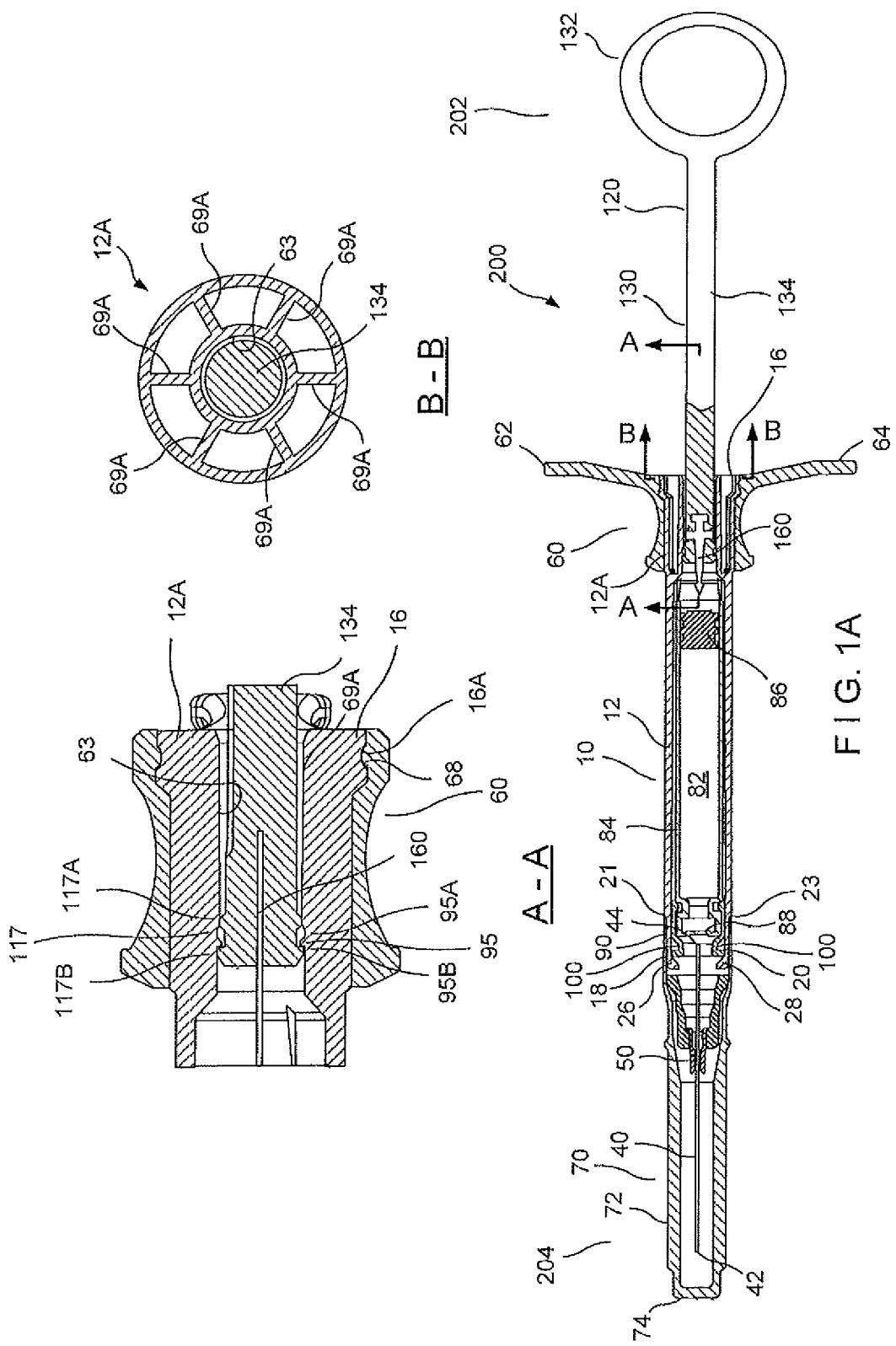

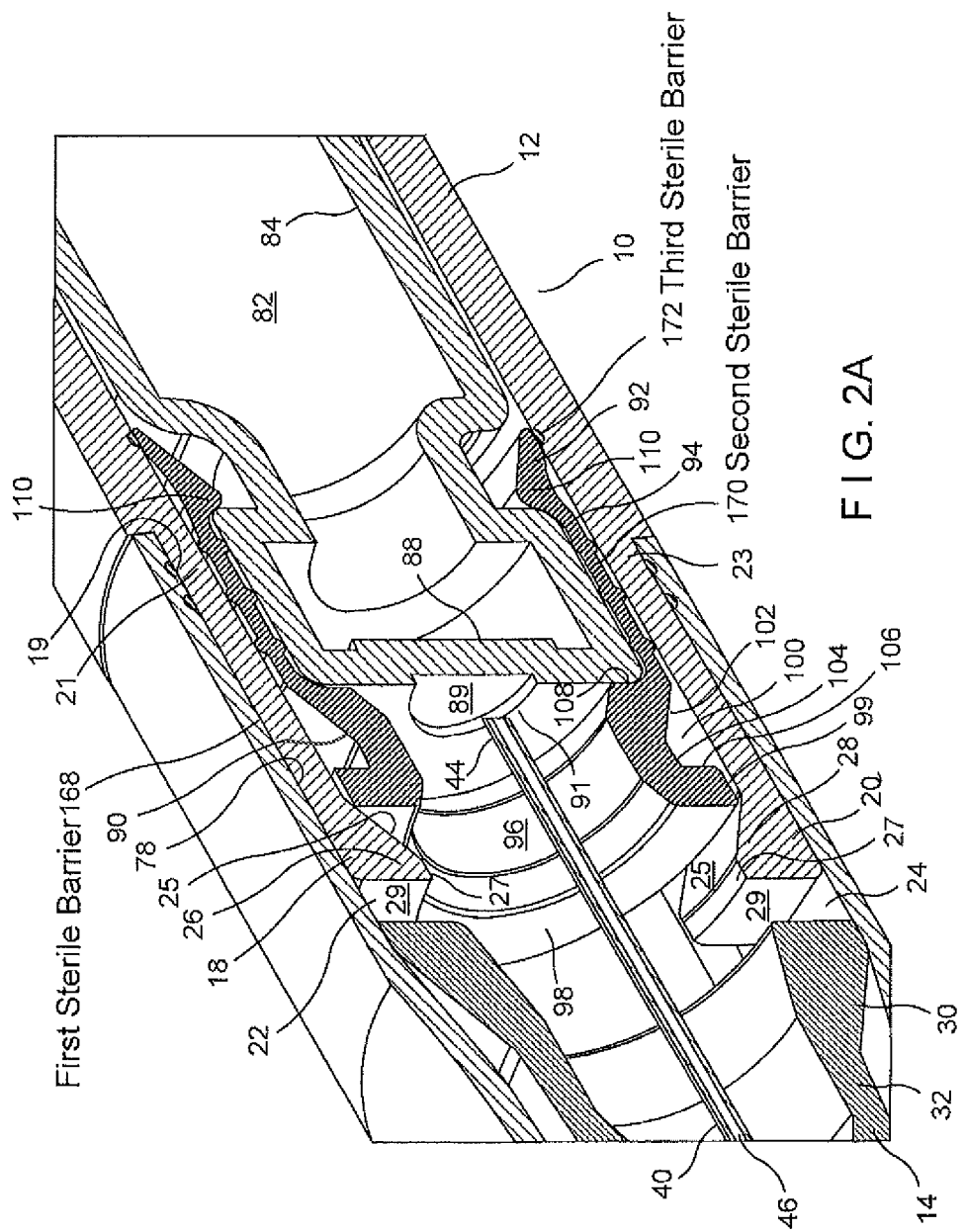
F I G. 2A

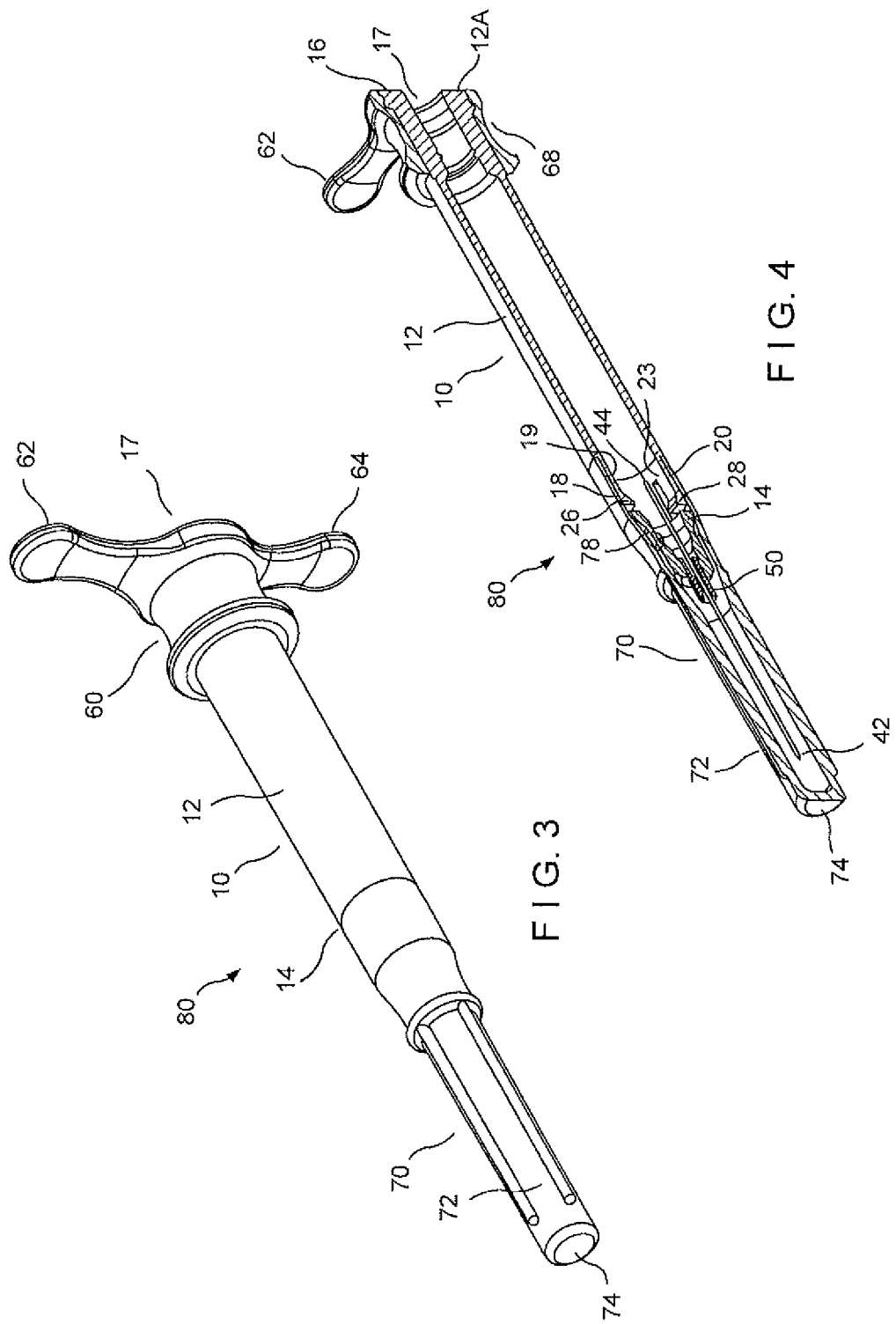

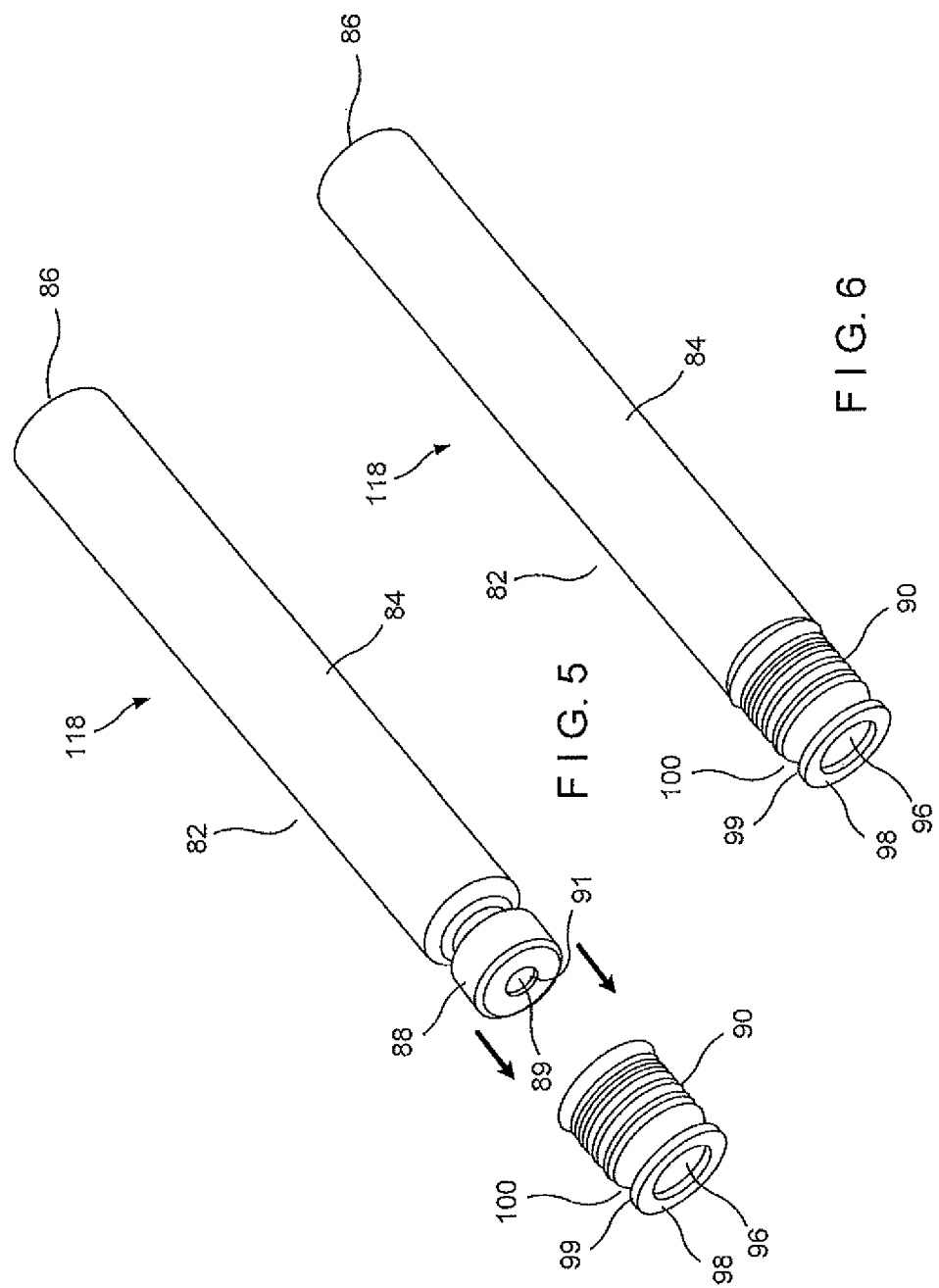

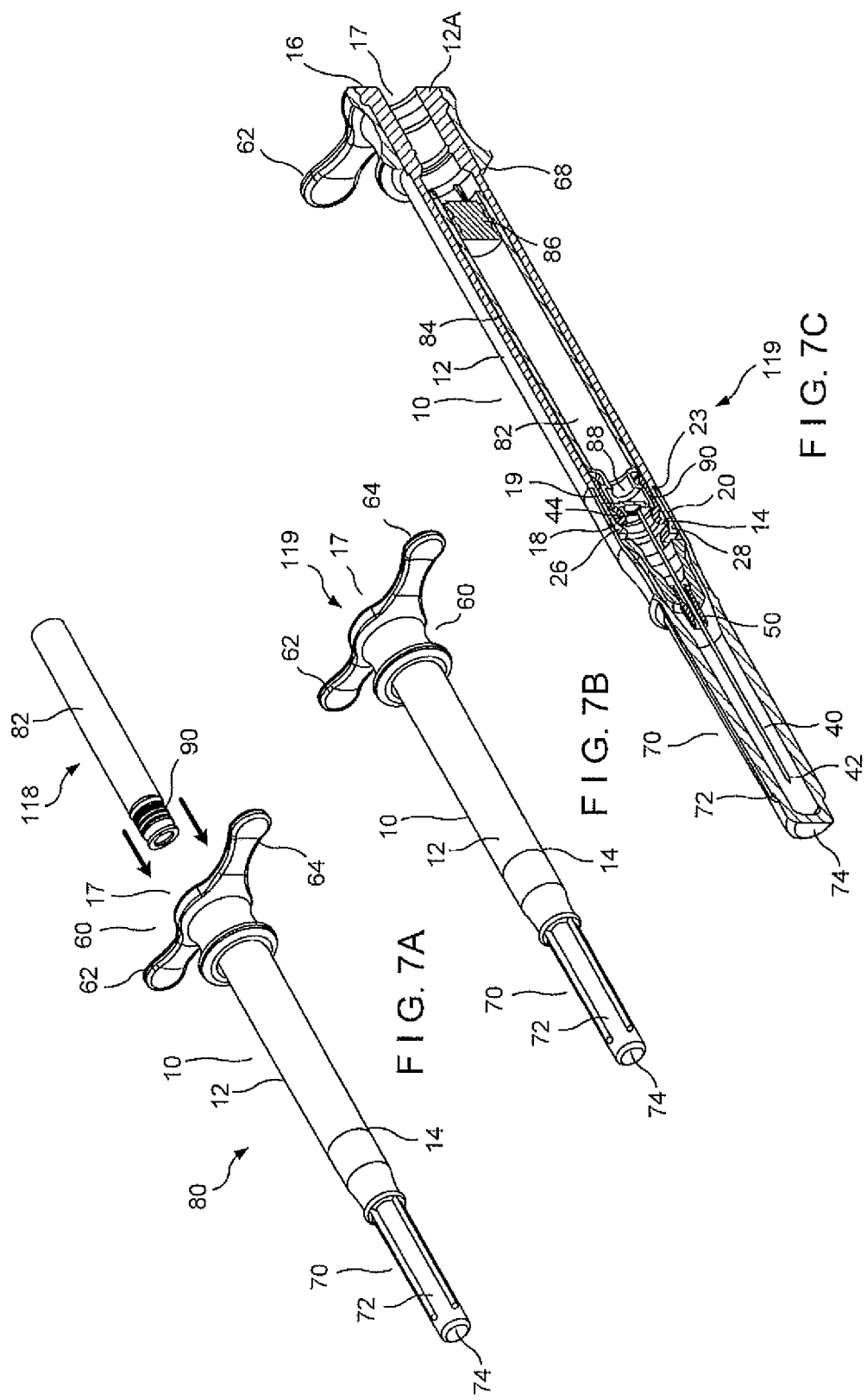

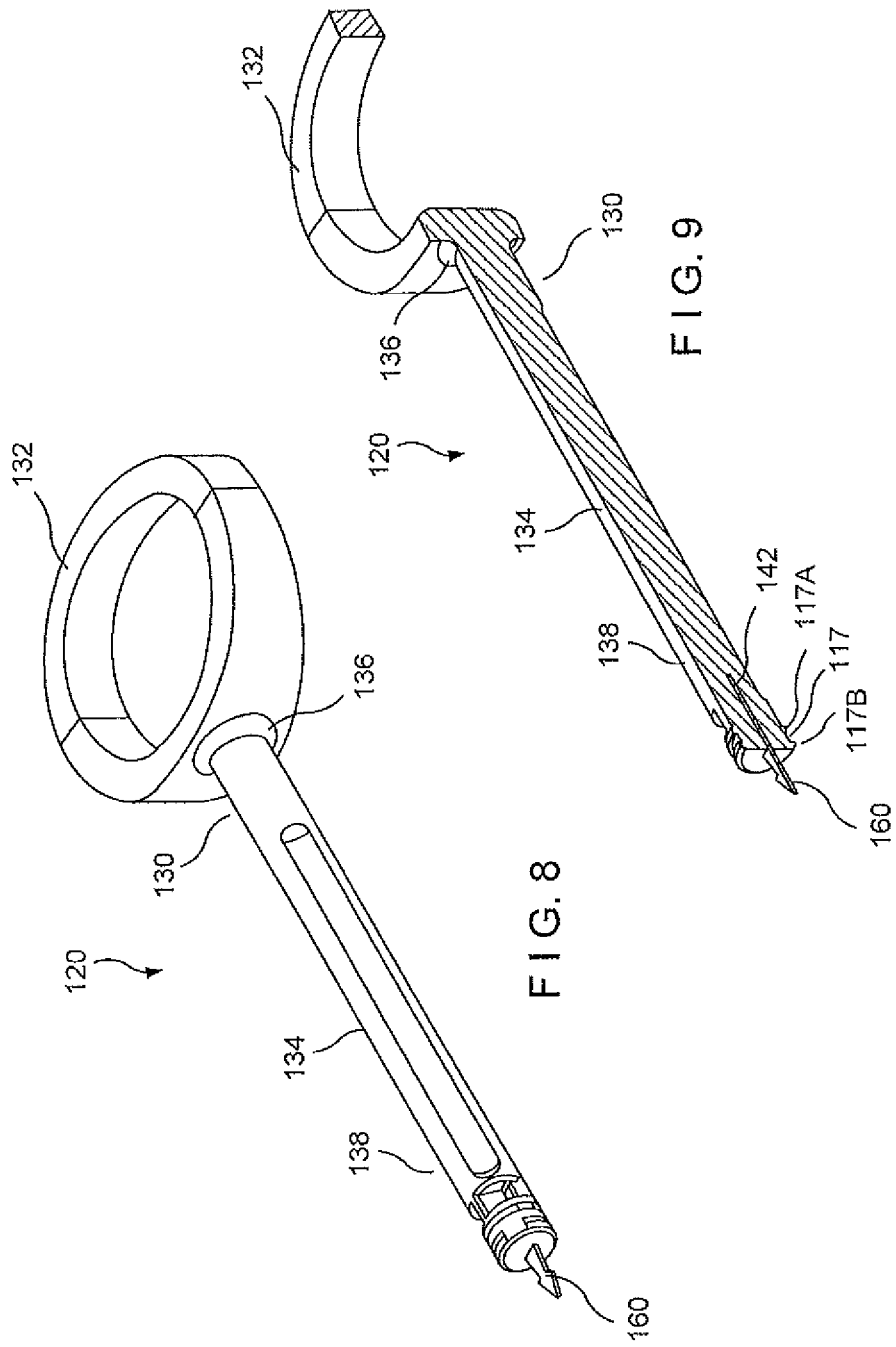

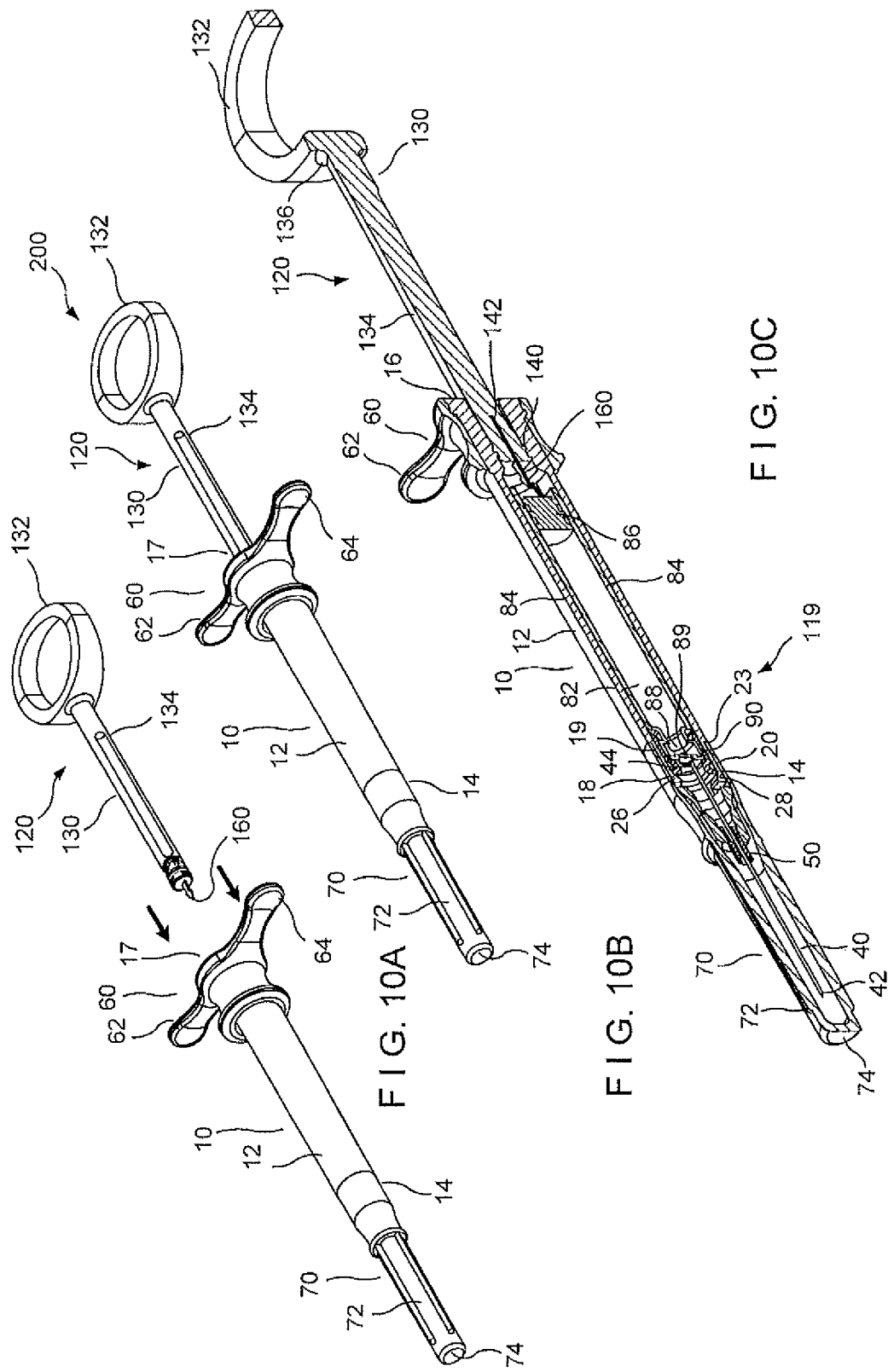

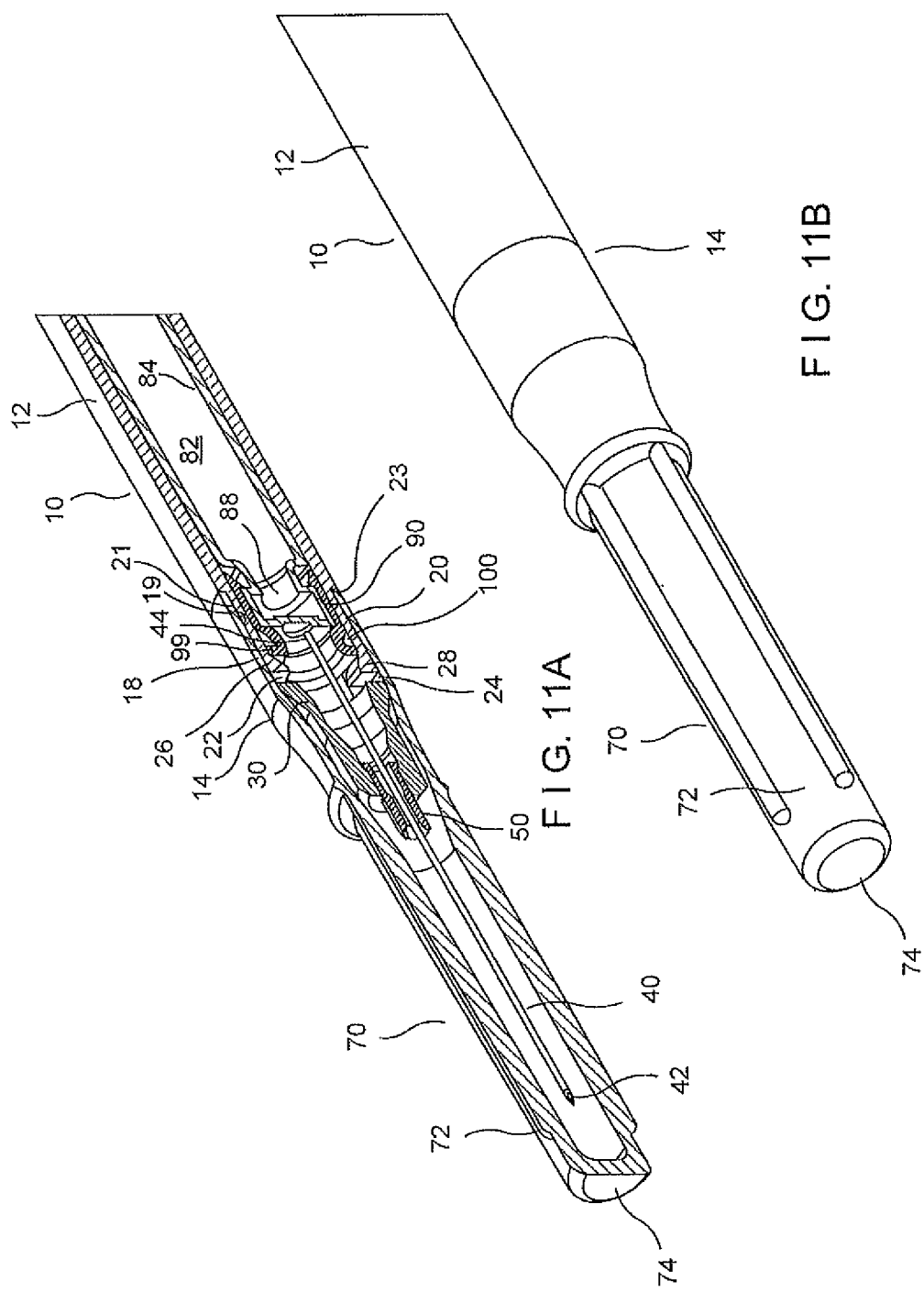

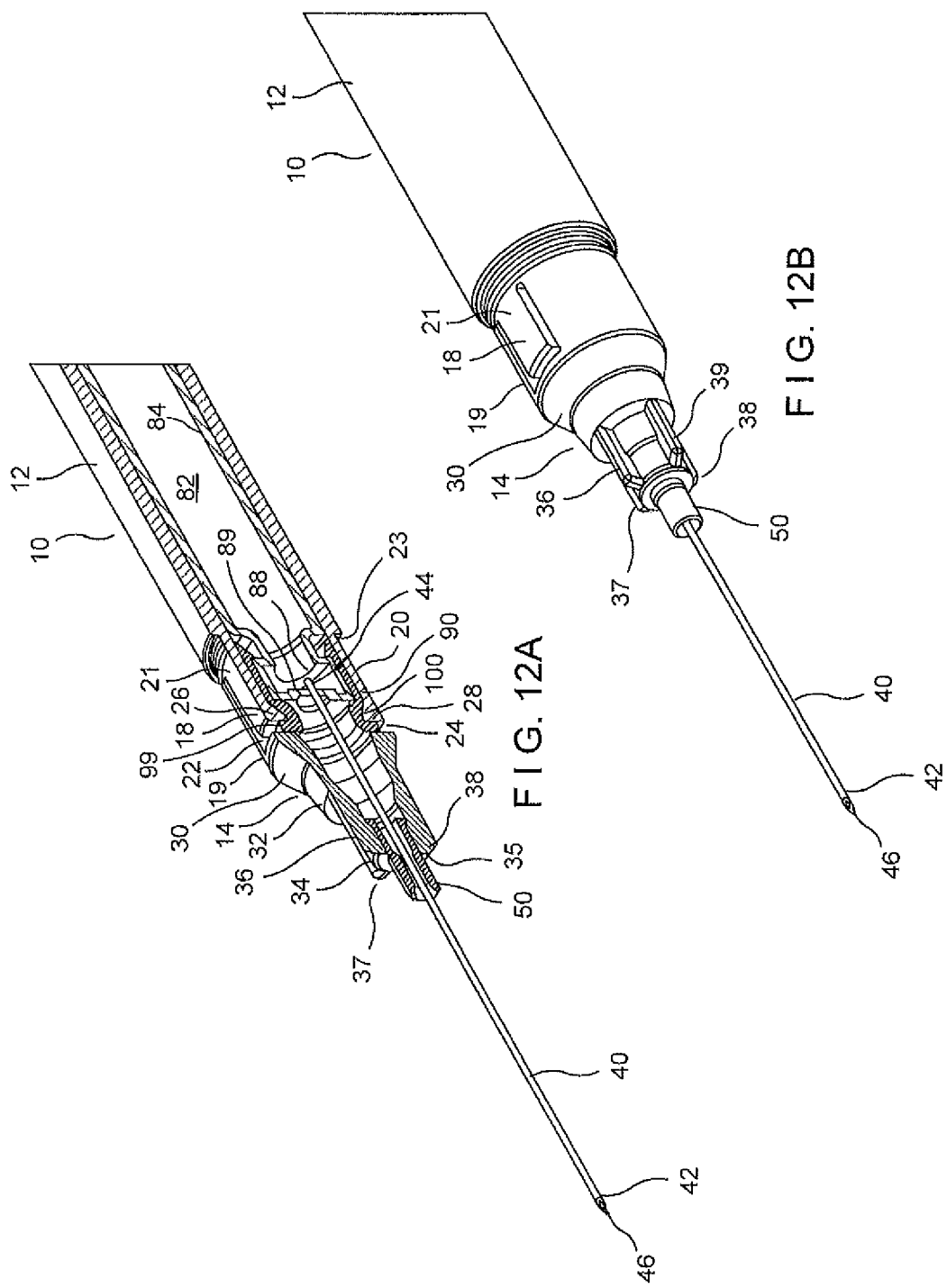

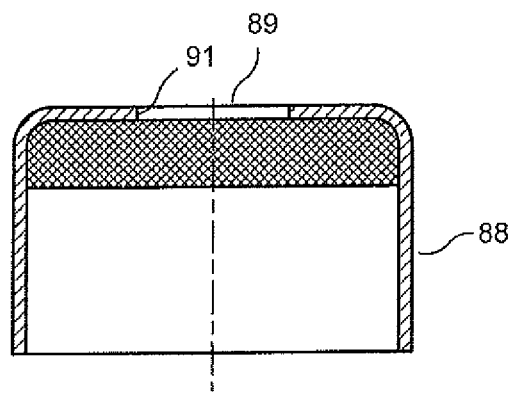
F I G. 13A
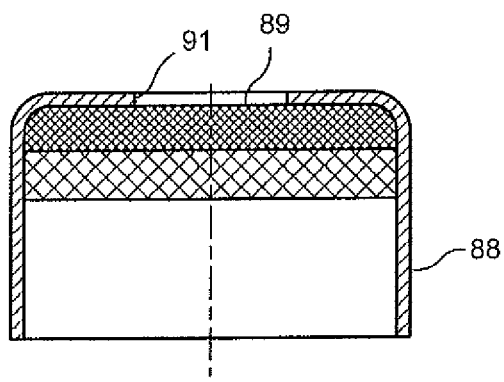
F I G. 13B

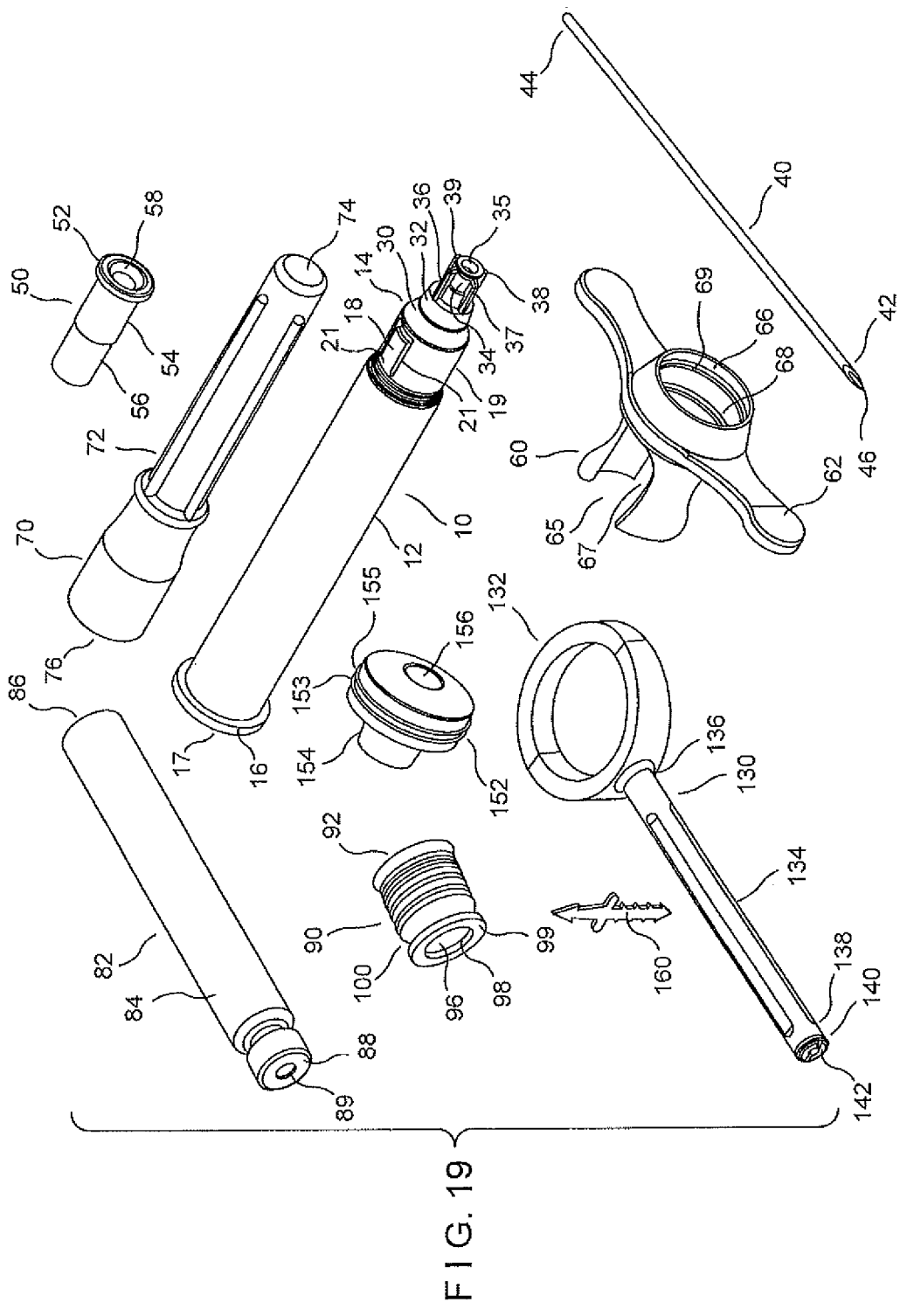

SEALED SELF-ACTIVATING INJECTION DEVICE FOR DELIVERY OF MEDICINE FROM A PREFILLED CARTRIDGE OR VIAL

This application claims priority under 35 U.S.C. 119(e) of U.S. Provisional Patent Application Ser. No. 61/875,274, filed on Sep. 9, 2013, the disclosure of which is incorporated by reference herein in its entirety.

BACKGROUND

The present disclosure relates to a syringe or similar injection device, which is configured to inject an injectable agent from a pre-loaded cartridge, in a single-use configuration.

Conventionally, syringes for the sterile injection of injectable agents in the medical, dental or veterinary fields are filled with the injectable agent by a medical professional just prior to use. However, conventional prior art syringes may be problematic in that they may place the medical professional at a higher risk for an accidental needle stick due to the handling before and after the injection.

SUMMARY

It is therefore an object of the present disclosure to provide improvements in syringe-type injection devices, particularly pre-loaded single-use, disposable devices containing a needle and a cartridge containing an injectable agent, wherein the injection device has an armed and a pre-armed state.

It is therefore a further object of the present disclosure to provide improvements in syringe-type injection devices which are particularly adaptable to sterile injection of injectable agents, wherein the injection device has an armed and a pre-armed state.

These and other objects are attained by providing a sterile injector assembly, pre-loaded with an injectable agent. The sterile needle assembly includes a stainless steel cannula set within a hub with a needle sheath, bulk packaged and sterilized by gamma ray or ultra-violet irradiation or a similar process as appropriate to the design.

More particularly, taught herein is a disposable and sterile pre-loaded injection device comprising a cartridge with a closed first cartridge end and a second cartridge end including a cartridge plunger, a housing enclosing the cartridge, the housing including cantilevered locking tabs, a needle, an adapter engaging the first cartridge end and further including an adapter engagement element, wherein the adapter is movable with respect to the cantilevered locking tabs, between a pre-armed position wherein the needle is separated from the cartridge and an armed position wherein the needle penetrates the septum of the cartridge.

Additionally, taught herein is a method of manufacture of an injection device including the steps of engaging a sterile cartridge to a sterile adapter, loading the sterile cartridge with the sterile adapter into a housing, and securing the sterile cartridge with the sterile adapter within the housing.

In order to use the device, the medical professional (which may include a dental, veterinary or similar professional) removes the device from the packaging, engages the plunger rod in some embodiments, removes the needle sheath (thereby removing the constraints on the outward flexure of the cantilevered locking tabs) and depresses the plunger rod. Movement of the plunger rod causes the cartridge assembly to move forward relative to a fixed or stationary housing thereby flexing the cantilevered locking tabs outwardly and advancing the septum into the butt end of the cannula thereby reaching the armed or detent position, creating a sterile fluid path for the injectable agent and allowing the injectable agent of the cartridge to be dispensed. In this armed or detent position, the cartridge assembly is locked in place by the cantilevered locking tabs and cannot be detached or retracted during aspiration.

BRIEF DESCRIPTION OF THE DRAWINGS

Further objects and advantages of the disclosure will become apparent from the following description and from the accompanying drawings, wherein:

FIG. 1A is a cross-sectional view of the assembled injection device of the present disclosure in the pre-armed configuration, including cross-sectional areas of detail along plane A-A and plane B-B.

FIG. 2A is a perspective cut-away view in detail, showing the cartridge-to-housing interface and its relation to the surrounding components in the pre-armed configuration of the injection device of the present disclosure.

FIG. 3 is a perspective view of a partially assembled injection device of the present disclosure, prior to the insertion of the cartridge and plunger assembly.

FIG. 4 is a partially cut-away view corresponding to FIG. 2.

FIG. 5 is a perspective partially exploded view illustrating the attachment of the cartridge-to-housing interface to the cartridge of the present disclosure.

FIG. 6 is a perspective view of the assembly of the cartridge-to-housing interface and the cartridge of the present disclosure.

FIG. 7A illustrates the insertion of the assembled cartridge-to-housing interface and cartridge of FIGS. 5 and 6 into the partially assembled injection device of FIG. 3, of the present disclosure.

FIG. 7B is a perspective view of the partially assembled injection device of the present disclosure, containing the cartridge-to-housing interface and cartridge of FIGS. 5 and 6.

FIG. 7C is a perspective cut-away view corresponding to FIG. 7B.

FIG. 8 is a perspective view of the plunger assembly of the present disclosure.

FIG. 9 is a perspective cut-away view of the plunger assembly of the present disclosure.

FIG. 10A illustrates the insertion of the plunger rod assembly of FIGS. 7 and 8 into the partially assembly injection device of FIGS. 9A, 9B and 9C of the present disclosure.

FIG. 10B is a perspective view of the fully assembled injection device of the present disclosure in the pre-armed configuration.

FIG. 10C is a perspective cut-away view corresponding to FIG. 10B.

FIG. 11A is a further perspective cut-away view, showing the cartridge-to-housing interface and its relation to the surrounding components in the pre-armed configuration of the injection device of the present disclosure.

FIG. 11B is a perspective view of the needle sheath and surrounding components of the injection device of the present disclosure, the needle sheath constraining the injection device to the pre-armed configuration.

FIG. 12A is a perspective cut-away view, showing the cartridge-to-housing interface and its relation to the surrounding components in the armed or detent configuration of the injection device of the present disclosure, with the septum of the cartridge punctured.

FIG. 12B is a perspective view corresponding to FIG. 12A.

FIGS. 13A and 13B are cross-sectional views of the cap and septum of the present disclosure.

FIG. 19 is an exploded view of the components of the alternative embodiment of the injection device of FIGS. 17 and 18.

DETAILED DESCRIPTION

Figure 1B:
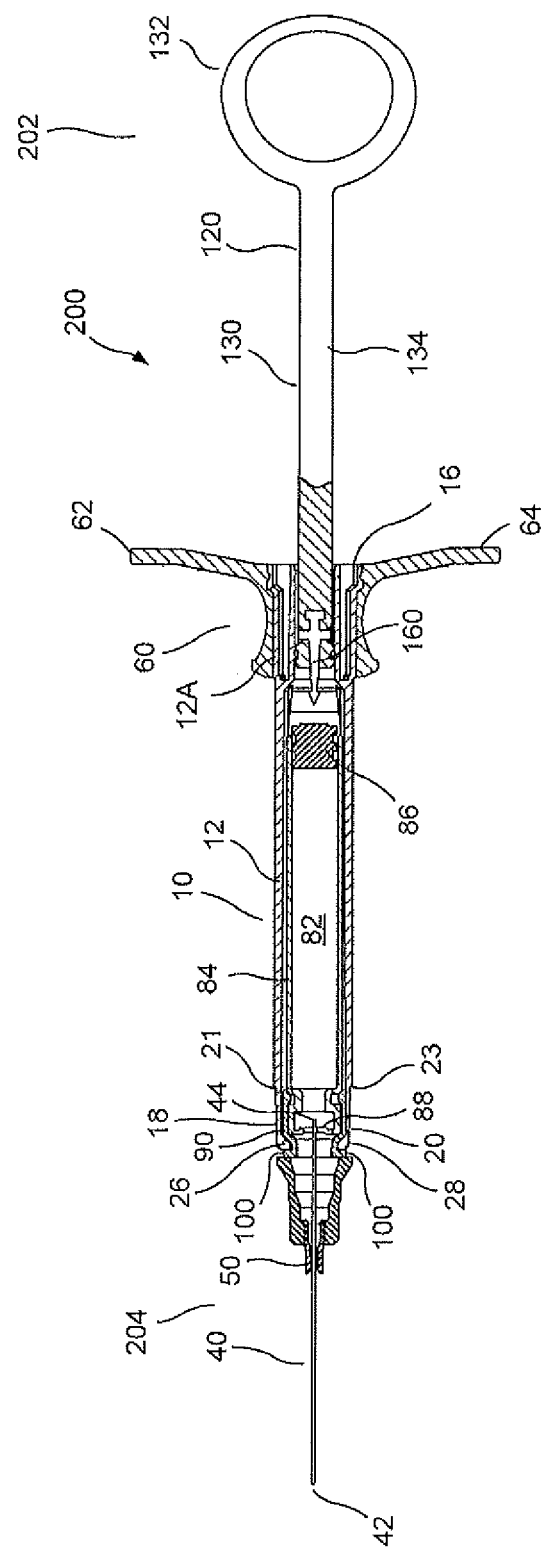
FIG. 1B is a cross-sectional view of the assembled injection device of the present disclosure in the armed configuration.

Disclosed herein are pre-loaded syringe assemblies with a plurality of sterility barriers and aseptic methods of manufacturing the same. The pre-loaded syringe assemblies include a plurality of sterility barriers to maintain the sterility of certain components of the syringe assemblies during packaging, shipping and storage until use by a medical professional. The pre-loaded syringe assemblies taught herein are shipped to a medical professional in a pre-armed state while maintaining sterility of the contents of a pre-loaded cartridge and the surfaces of components that will come into contact with the contents of the cartridge. Prior to use of the pre-loaded syringe assemblies taught herein a medical professional places the assembly in an armed state by forming a sterile fluid pathway between a needle tip and the contents of the cartridge. Placement of the assembly into the armed state occurs by placing pressure on a terminal end of a plunger to move the cartridge toward a distal end of the assembly and cause a butt end of the needle to pierce a septum attached to the cartridge. During arming, the cartridge and the plunger move distally relative to a fixed housing.

Referring now to the drawings in detail wherein like numerals indicate like elements throughout the several views, one sees that the injection device 200 is a single-patient, single-use, disposable, sterile injection device pre-loaded with an injectable agent. As used herein, the term "injectable agent" refers to, but is not limited to, local anesthetics, therapeutic or pharmaceutical agents, cosmetic agents or other liquids, gels or powders in the medical, dental, veterinary or cosmetic fields. Further, one sees that FIG. 1A is a cross-sectional view of the fully assembled injection device 200, with a proximal end 202 and a distal end 204, in a pre-armed state (i.e., a sterility barrier of the cartridge 82 has not been pierced by the butt end 44 of the needle cannula 40 prior to the formation of a continuous sterile pathway from the cartridge 82 to the tip 42 of needle cannula 40 to inject the injectable agent), with a cartridge 82 concentrically surrounded by housing 10. The cartridge 82 includes a cartridge plunger 86 on one end and a cap or band 88 on the other end that secures a septum 89 thereto. The septum 89 forms one sterility barrier to maintain sterility of a liquid held in the cartridge 82. A cartridge-to-housing interface 90 engages the cap 88 of the cartridge 82. The housing 10 includes first and second cantilevered locking tabs 18, 20 which are constrained from outward flexure by the outward concentric engagement of the needle sheath 70. The cantilevered first and second locking tabs 18, 20, in this constrained position, prevent the forward movement of the cartridge-to-housing interface 90 and the cartridge 82 thereby maintaining a separation between the butt end 44 of the cannula 40 and the septum 89 of cartridge 82 held in place by cap or band 88 Often, the harpoon 160 is visible through the housing, allowing the medical professional visualization of the harpoon 160. Moreover, the length of housing 10 which provides for the visibility of the harpoon 160 further often provides for improved axial control of the injection device 200 during operation.

In the armed state (i.e., piercing of the sterility barrier by the butt end 44 of the needle cannula 40 to form a continuous sterile pathway from the cartridge 82 to the tip 42 of cannula 40 to inject the injectable agent) of injection device 200, which is illustrated in FIG. 1B, the needle sheath 70 has been removed thereby allowing outward flexure of the first and second locking tabs 18, 20 and further allowing the cartridge 82 and cartridge-to-housing interface 90 to be moved forward toward the distal end 204 by motion on the plunger rod 130 so that the butt end 44 of the cannula 40 penetrates the septum 89 of the cartridge 82. As the cartridge 82 and cartridge-to-housing interface 90 are moved forward relative to the fixed housing 10, first and second latching bosses 26, 28 engage the annular notch 100 of the cartridge-to-housing interface 90. In this armed state, the injection device 200 is ready for use by a medical professional. It should be noted that while the first and second latching bosses 26, 28 are illustrated as being inwardly extending, that it is envisioned that this disclosure, particularly regarding latching and engagement elements, could encompass many different equivalent structures, for example, detents, stops, latches, catches and the like.

Figure 1C:
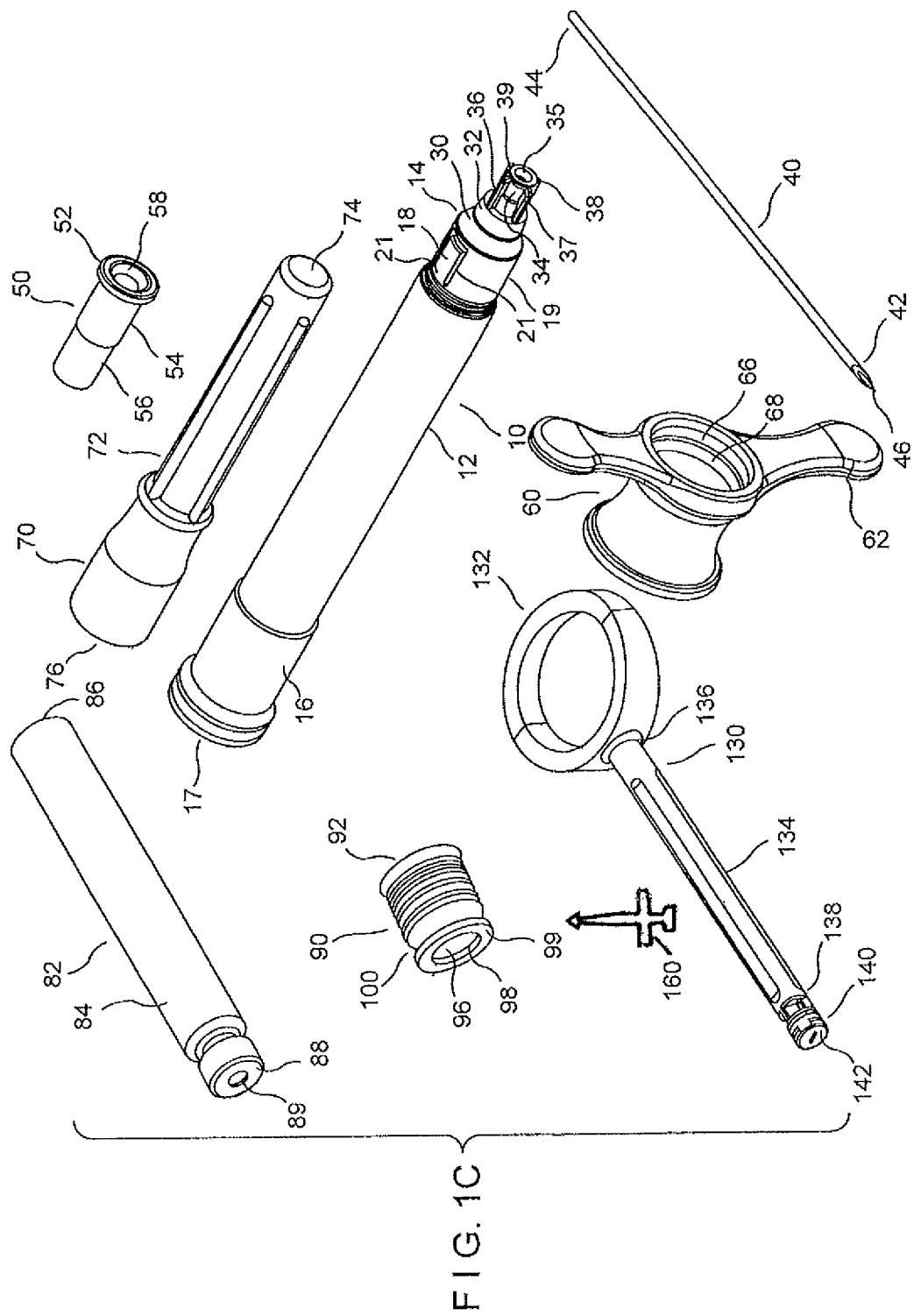
FIG. 1C is a perspective view of the various disassembled elements of the injection device of the present disclosure.

FIG. 1C illustrates the various components for the assembly of injection device 200. The housing 10, which can be seen in further detail in cut-away in FIGS. 1A (including areas of cross-sectional detail A-A and B-B), 1B, 2A, 2B, 4, 7C, 10C, 11A, and 12A, is made from hard polyethylene or polypropylene, but is not limited thereto, and includes a cylindrical body 12 with a forward nose 14 and a mounting hub 12A of somewhat increased diameter on its proximal end. a passageway 63 of reduced diameter passing therethrough for receiving the plunger rod assembly 120 as shown in FIGS. 8 and 9. Mounting hub 12A further includes radially oriented internal fins 69A between the interior wall of mounting hub 12A and the exterior wall of passageway 63 (see cross-sectional area of detail B-B of FIG. 1A). Mounting hub 12A further includes an annular lip 16 with an annular groove 16A formed thereon for mounting or rotatably engaging the finger flange assembly 60 (see the area of cross-sectional detail A-A of FIG. 1A as well as FIGS. 7A-7C). The finger flange assembly is often rotatably mounted, but other embodiments include a finger flange assembly which is fixed.

Figure 2B:
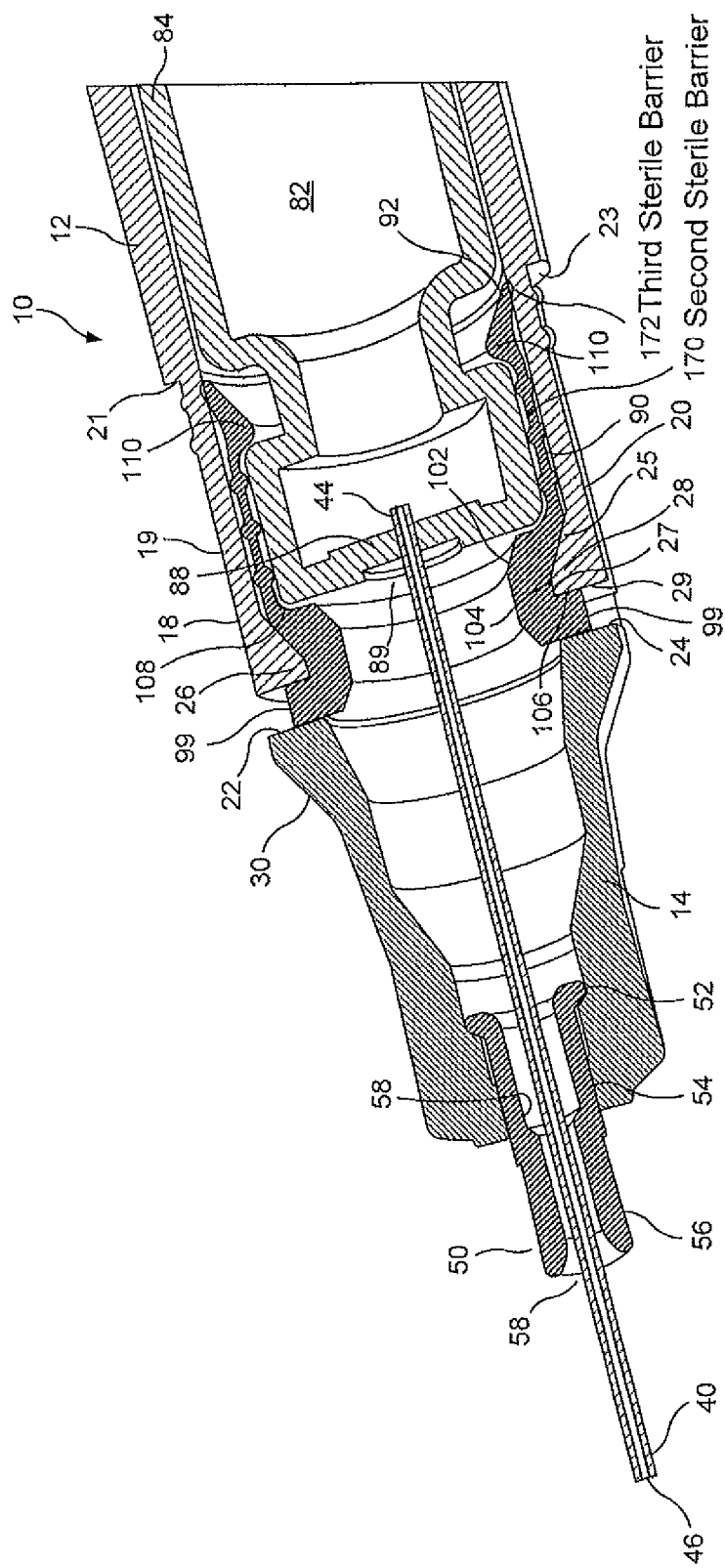
FIG. 2B is a perspective cut-away view in detail, showing the cartridge-to-housing interface and its relation to the surrounding components in the armed configuration of the injection device of the present disclosure.

The forward nose 14 of cylindrical body 12 includes a section 19 of reduced diameter which further includes the first and second cantilevered locking tabs 18, 20. As shown in FIG. 2A, the first and second cantilevered locking tabs 18, 20 are formed from and integral with the wall of section 19 of reduced diameter and defined by first and second channels 22, 24 cut on three sides of the first and second cantilevered locking tabs 18, 20 thereby forming respective first and second cantilevered integral connections 21, 23 with the section 19 of reduced diameter. Additionally, as shown in detail in FIGS. 2A and 2B, the interior forward end of first and second cantilevered locking tabs 18, 20 include first and second latching bosses 26, 28. As shown in the cut-away views of FIGS. 2A and 2B, the first and second latching bosses 26, 28 each include a ramped portion 25, a flat distal portion 27 and a transverse orthogonal wall 29. The forward nose 14 further includes a frustoconical section 30 leading to first cylindrical portion 32 which, in turn, leads to cylindrical wall 34 forming cannula passageway 35. Four support wall segments 36, 37, 38, 39 radially extend from cylindrical wall 34.

Needle cannula 40 is of conventional structure, made from stainless steel or a similar material, but not limited thereto, with a beveled pointed forward end 42 for insertion into a patient or other injection point, a rear or butt end 44 for receiving an injectable agent, and a central passageway 46.

Cannula crimp insert 50, made from stainless steel or a similar material, but not limited thereto, includes a rearward rimmed base 52 along with first and second cylindrical portions 54, 56, wherein first cylindrical portion 54 has a slightly greater diameter than second cylindrical portion 56 in order to seat within the interior of nose 14 of housing 10. Cannula crimp insert 50 further includes central passageway 58 for receiving and engaging needle cannula 40.

Finger flange assembly 60 is formed from injection molded plastic, but is not limited thereto, and may have no sterility requirement. Finger flange assembly 60 has two finger flanges 62, 64 for use by the medical practitioner during injection and further has a central bore 66 with an internal annular ridge 68 for engaging annular groove 16A of annular lip 16 of mounting hub 12A of housing 12 thereby providing for a snap fit with rotatable engagement between the finger flange assembly 120 and the mounting hub 12A which allows the user or medical practitioner to orient the bevel 42 of the needle cannula 40 during use. Bevel orientation can be achieved in other ways, such as, but not limited to, a fixed finger flange assembly in combination with either a rotating plunger rod or a plunger rod with a rotating harpoon.

Needle sheath 70 includes a generally cylindrical wall 72 with a closed end 74 and an open end 76. The sheath 70 is formed from polyethylene or polypropylene, but is not limited thereto. The interior of cylindrical wall 72 immediately inwardly adjacent from open end 76 includes an internal contour 78 to outwardly concentrically engage the following portions of housing 10, section 19 of reduced diameter, frustoconical section 30, first cylindrical portion 32 and wall segments 36, 37, 38, 39. While the needle sheath 70 is mounted on housing 10 thereby forming first sterile barrier 168 extending circumferentially around the outer diameter of section 19 of reduced diameter as it contacts the inner diameter of sheath 70 as shown in FIG. 2A, the concentric engagement of internal contour 78 of needle sheath 70 to section 19 of reduced diameter of housing 10 prevents the outward flexure of the first and second cantilevered locking tabs 18, 20 of the housing 10.

FIGS. 3 and 4 illustrate the axial relationship and configuration of housing 10, needle cannula 40, cannula crimp insert 50, finger flange assembly 60 and needle sheath 70 in order to achieve initial subassembly 80. The needle cannula 40 is inserted into cannula crimp insert 50. Thereafter, the cannula crimp insert 50, with the needle cannula 40 therein, is inserted through the rear opening 17 of housing 10 and inserted so as to be engaged within cannula passageway 35 within the forward nose 14 of housing 10. Alternatively, the needle cannula 40 may be directly secured to the housing 10 by an adhesive bond or a similar method thereby eliminating the cannula crimp insert 50. The needle sheath 70 is mounted on housing 10 so as to outwardly concentrically engage section 19 of reduced diameter, frustoconical section 30, first cylindrical portion 32 and wall segments 36, 37, 38, 39 of housing 10. Finger flange assembly 60 is mounted on housing 10 by engaging annular ridge of 68 of finger flange assembly 60 to annular groove 16A of annular lip 16 of mounting hub 12A. The initial subassembly 80 of FIGS. 3 and 4 is bulk sterilized either before or after assembly, by ultra-violet, gamma ray or a similar method as appropriate to the design.

FIGS. 5 and 6, as well as FIG. 1C, illustrate the axial relationship and configuration of the cartridge 82 and the cartridge-to-housing interface 90. As shown in the cut-away view of FIG. 7C, the cartridge 82 includes cylindrical glass wall 84, containing the injectable agent therein, and further includes a cartridge plunger 86 at one end and an aluminum cap or band 88 at the other end, holding a septum 89 in place.

The cartridge-to-housing interface 90 is formed from hard polyethylene or polypropylene, but is not limited thereto, and includes a first end 92 with cylindrical wall 94 for forming a tight fit around the cap 88 of cartridge 82, holding septum 89 in place. As shown in FIGS. 13A and 13B, the cap 88 holds the septum 89 in place (FIG. 13A discloses a single layer septum 89 while FIG. 13B discloses a dual layer septum 89), exposed through opening 91 in cap 88. The combination of the cap 88 and the septum 89 form a piercable sterility barrier to maintain sterility of the contents of the pre-loaded cartridge 82. Cartridge-to-housing interface 90 further includes a central passageway 96 for communication between the first end 92 and second end 98. Second end 98 includes outwardly flared edge 99. Immediately inwardly adjacent from second end 98, annular notch 100 is formed. As shown in the cut-away views of FIGS. 2A and 2B, annular notch 100 has a ramped portion 102, an interior flat portion 104 and a transverse annular wall section 106 to correspond or to be complementary to the ramped portion 25, flat distal portion 27 and transverse orthogonal wall 29 of first and second latching bosses 26, 28 of housing 10. Additionally, as shown in FIGS. 2A and 2B, an annular ridge 108 is formed interiorly adjacent from annular notch 100 in order to form a seat for the cap 88 of cartridge 82. Similarly, annular lip 110 is formed on the interior of cylindrical wall 94, immediately inwardly adjacent from first end 92 to snap engage the cap 88 of cartridge 82.

As shown in FIGS. 5 and 6, the cartridge-to-housing interface 90 (which has been bulk sterilized by gamma ray, ultra-violet or a similar method as appropriate to the design) and cartridge 82 are brought into a controlled area (laminar airflow ISO class air supply). During bulk sterilization, the cartridges 82 are oriented vertically with the cap 88 on top and have their top surface sterilized with pulsed ultra-violet light or by a similar method. The cartridge-to-housing interface 90 is then pressed onto the cap 88 as shown in FIGS. 5 and 6 whereby the interior of cylindrical wall 94 of the first end 92 of the cartridge-to-housing interface 90 forms a friction fit with the cap 88 of cartridge 82 thereby forming second sterile barrier 170, extending circumferentially around the cap 88 as it contacts the interior of cylindrical wall 94 (see FIGS. 2A and 2B) of the cartridge-to-housing interface 90 providing a maximum insertion, and a seat for the cartridge 82 while annular lip 110 of the cartridge-to-housing interface 90 snap engages the cap 88 of cartridge 82. This results in second subassembly 118.

As shown in FIGS. 7A, 7B, and 7C, the cartridge subassembly 118, comprising the cartridge 82 with the cap 88 engaged by the cartridge-to-housing interface 90, is inserted into the initial subassembly 80 through the rear opening 17 of housing 10 thereby achieving the configuration of the injector subassembly 119 of FIGS. 7B and 7C. In the configuration of FIG. 7C, and as shown in detail in FIG. 2A, the first and second latching bosses 26, 28 of first and second cantilevered locking tabs 18, 20, which are prevented from outward deflection by the needle sheath 70, provide a stop for the maximum insertion of the cartridge-to-housing interface 90 in this pre-armed configuration. Further, this maximum insertion of the cartridge-to-housing interface 90 provides for the butt end 44 of needle cannula 40 to be separated from the cap 88 and septum 89 of cartridge 82. Additionally, as shown in FIGS. 2A and 2B, third sterile barrier 172 is formed circumferentially around the cartridge-to-housing interface 90 as it the inner diameter of the housing 10.

Figure 16:
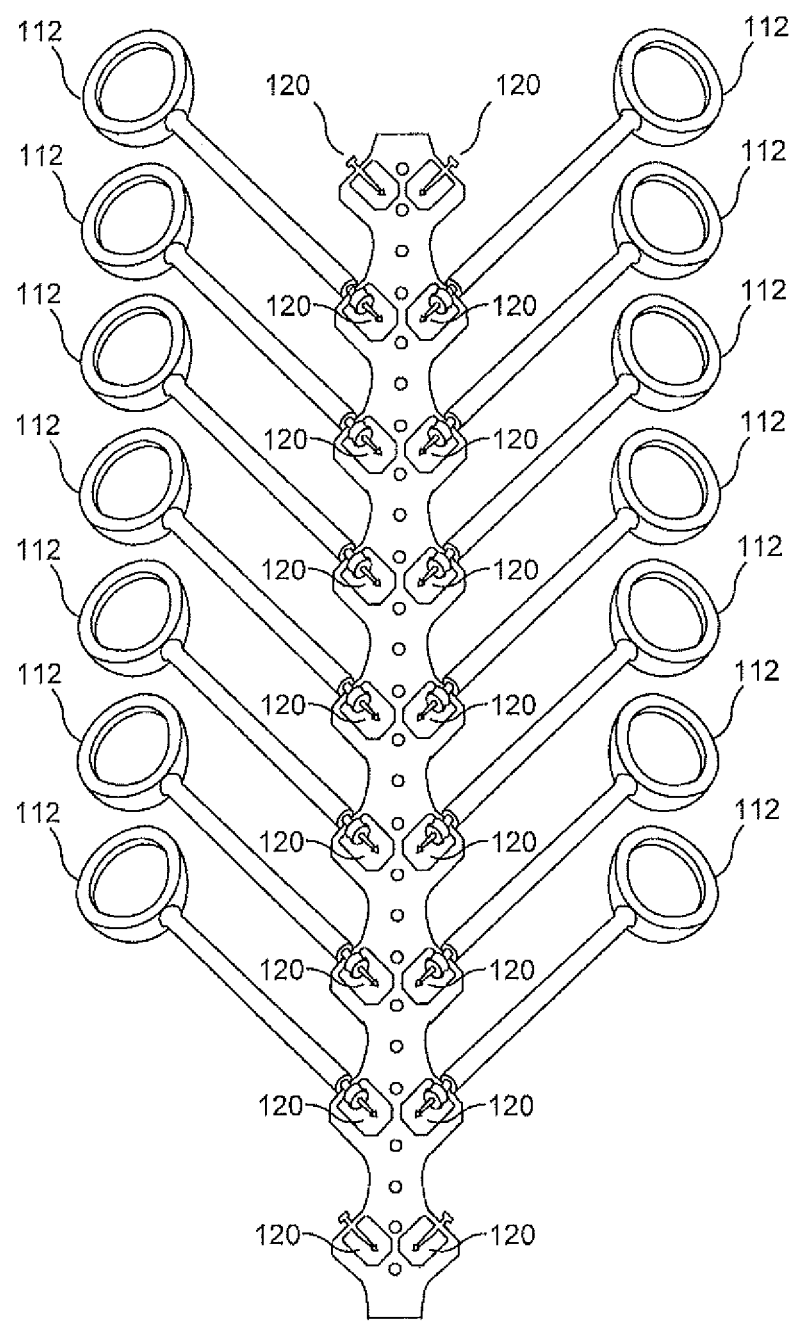
FIG. 16 is a diagram of a plunger assembly strip which may be used in the assembly of an embodiment of the present disclosure.

FIGS. 8 and 9 are illustrations of plunger rod assembly 120 which includes plunger rod 130 and harpoon 160. The plunger rod 130 is made from hard polyethylene or polypropylene, but are not limited thereto while the harpoon 160 is made from stainless steel or a similar material, but is not limited thereto. Plunger rod 130 includes circular thumb ring 132 and shaft 134. Shaft 134 includes proximal end 136 attached to circular thumb ring 132 and distal end 138 which includes annular retention channel 117 between annular ring 117A and distal annular terminating ridge 117B. Harpoon 160 extends from longitudinal blind bore 142 and, as shown in FIG. 10C, is separated from the cartridge plunger 86 when injection device is in the pre-armed configuration, but engages the cartridge plunger 86 when the injection device 200 is in the armed state and when the injection is being administered. The assembly of the harpoon 160 into the shaft 134 can be done in many different ways. For example, as depicted in FIGS. 8 and 9 the harpoon 160 may be press fit into a terminal end of the shaft 134. In another example depicted in FIG. 16, the harpoon 160 is insert molded as part of molding the shaft 134.

The plunger rod assembly 120 of FIGS. 8 and 9 is engaged within the mounting hub 12A as illustrated in the areas A-A and B-B of cross-sectional detail of FIG. 1A. An internal annular retention ring 95 is formed on the interior of passageway 63 for engaging with a corresponding external annular retention channel (see element 118, FIG. 8A) on the plunger rod assembly 120. The internal annular retention ring 95 has a cross section with a sloped surface 95A facing toward the proximal end or user end, in order to facilitate insertion of the plunger rod assembly 120, but with an abrupt orthogonal surface 95B toward the distal end in order to capture the plunger rod assembly 120 once it is inserted, and to resist any subsequent withdrawal of the plunger rod assembly 120. The annular retention channel 117 is formed on shaft 134 of plunger rod assembly 120 between annular ring 117A and distal annular terminating ridge 117B. When the shaft 134 of plunger rod assembly 120 is initially inserted into passageway 63, the distal end of plunger rod assembly 120 slides over the sloped surface 95A of internal annular retention ring 95 so that internal annular retention ring 95 is captured within annular retention channel 117 between annular ring 117A and distal annular terminating ridge 117B. Similarly, the relationship or contact between the opposing orthogonal surfaces of distal annular terminating ridge 117B and orthogonal surface 95B resists any subsequent withdrawal of the plunger rod assembly 120 from the passageway 63. Likewise, the relationship or contact between the sloped surface 95A of internal annular retention ring 95 and the annular ring 117A causes a snap detent engagement of the plunger rod assembly 120 which holds the plunger rod assembly 120 in place, but which allows the medical professional to press against the plunger rod assembly 120 to overcome the snap detent engagement, thereby often causing both audible and tactile feedback, with the plunger rod assembly 120 being driven into passageway 63.

Figure 15:
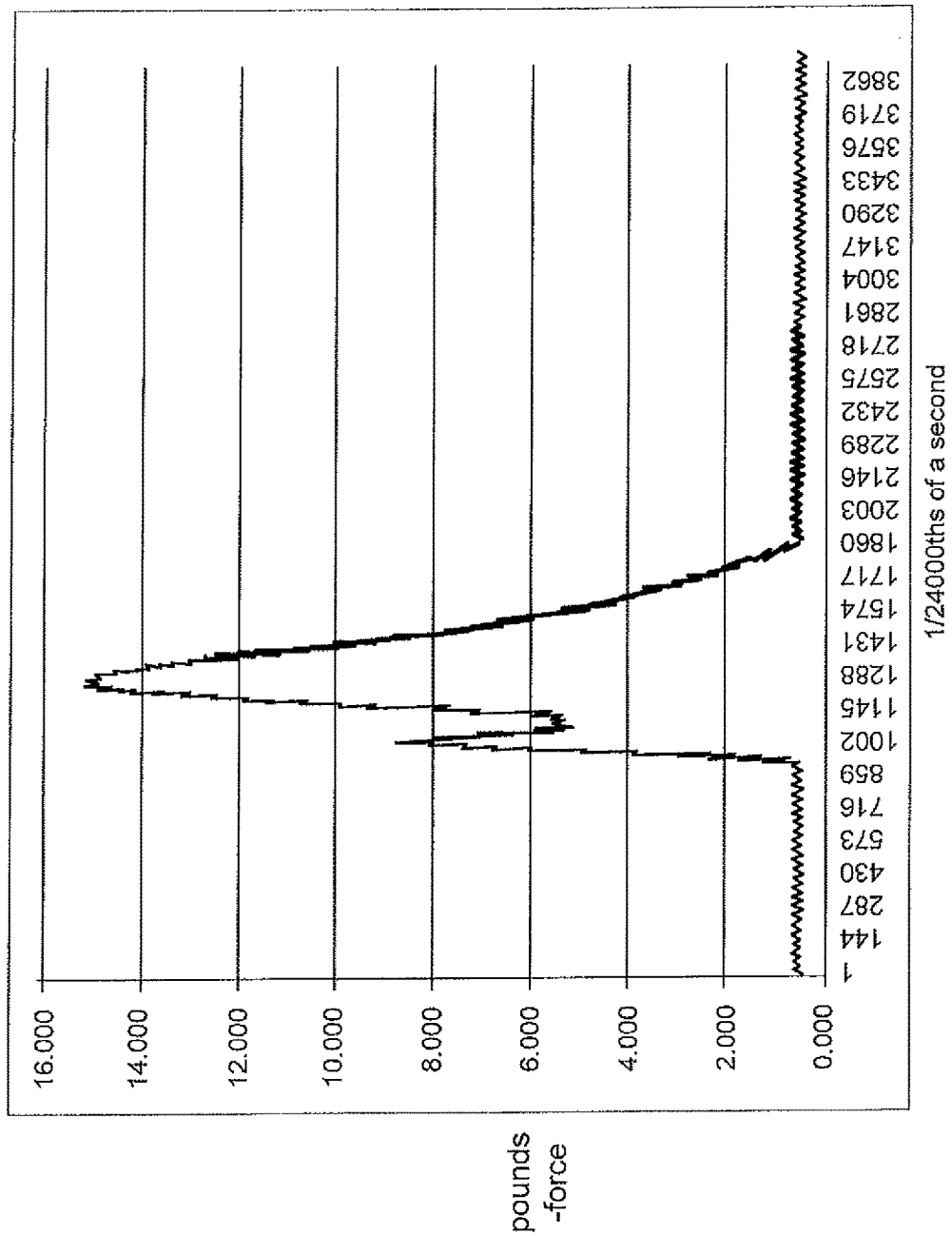
FIG. 15 is a chart of force versus time for a thumb ring and plunger of an embodiment of the present disclosure.

As shown in FIGS. 10A, 10B and 10C, the plunger rod assembly 120 is inserted into injector subassembly 119. In this inserted configuration of FIG. 10C, the configuration shown in the cross-sectional area of FIG. 1A is achieved. This configuration of the external annular channel 117 and the internal annular retention ring 95 often provides a tactile snap, as well as audible feedback, for the user while pushing the plunger rod assembly 120 to operate the injection device 200. FIG. 15 illustrates that as force or energy is applied, the snap detent configuration of internal annular retention ring 95 and external annular channel 117 holds the energy until approximately fifteen pounds-force is applied as shown on the Y-axis, whereas the X-axis is sample number, at a sampling rate of 24,000 samples per second. Then, disengagement of the detent configuration occurs, the momentum is momentarily released to allow the harpoon 160 to travel at a faster speed and force than would occur without the snap detent configuration. This is particularly a benefit for users who are not as likely to use an aggressive slap style of activation.

FIGS. 10B and 10C illustrate the injection device 200 in the pre-armed state as it is often provided to the customer in a flow wrapper package (not shown). In this pre-armed state, as shown in FIGS. 2A and 10C, the butt end 44 of needle cannula 40 is separated from the cap 88 and septum 89 of cartridge 82 and the harpoon 160 is separated from the cartridge plunger 86. In particular, as shown in FIG. 2A, this separation of the butt end 44 of the needle cannula 40 from the septum 89 of cartridge 82 is caused by the rigid positioning of first and second latching bosses 26, 28 of first and second cantilevered locking tabs 18, 20, as constrained by the needle sheath 18, providing a stop to the forward movement of the cartridge subassembly 118 comprising the cartridge-to-housing interface 90 and cartridge 82.

Figure 17:
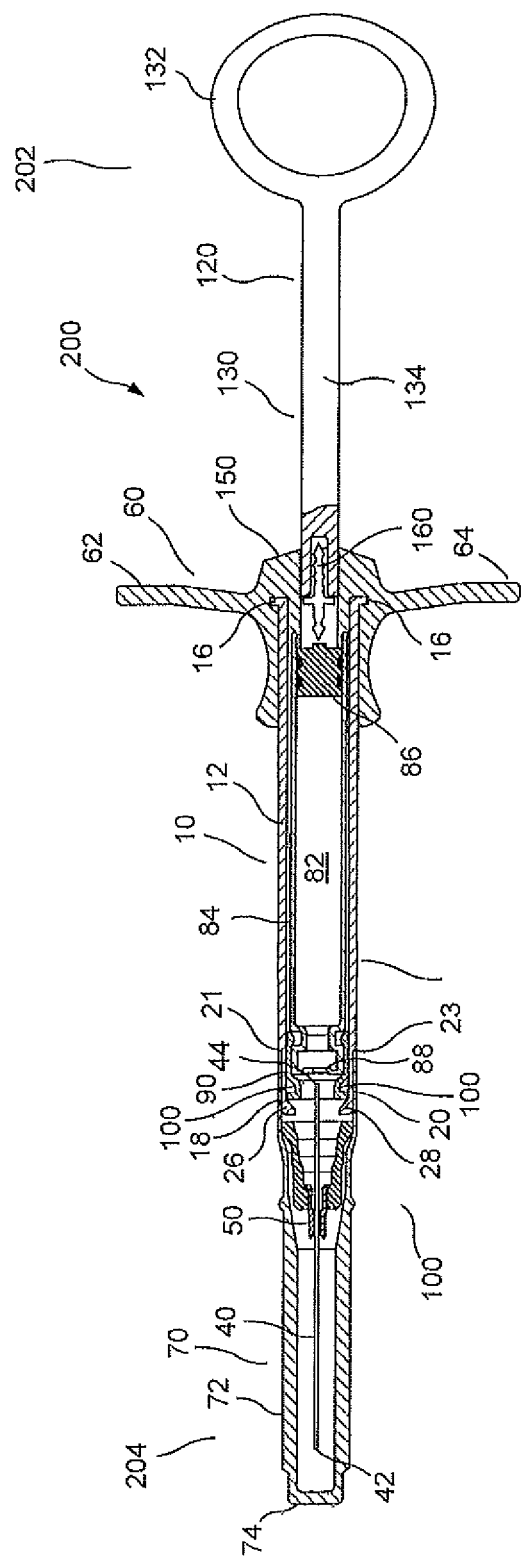
FIG. 17 is a cross-sectional view of an alternative embodiment of the assembled injection device of the present disclosure in the pre-armed configuration.
Figure 18:
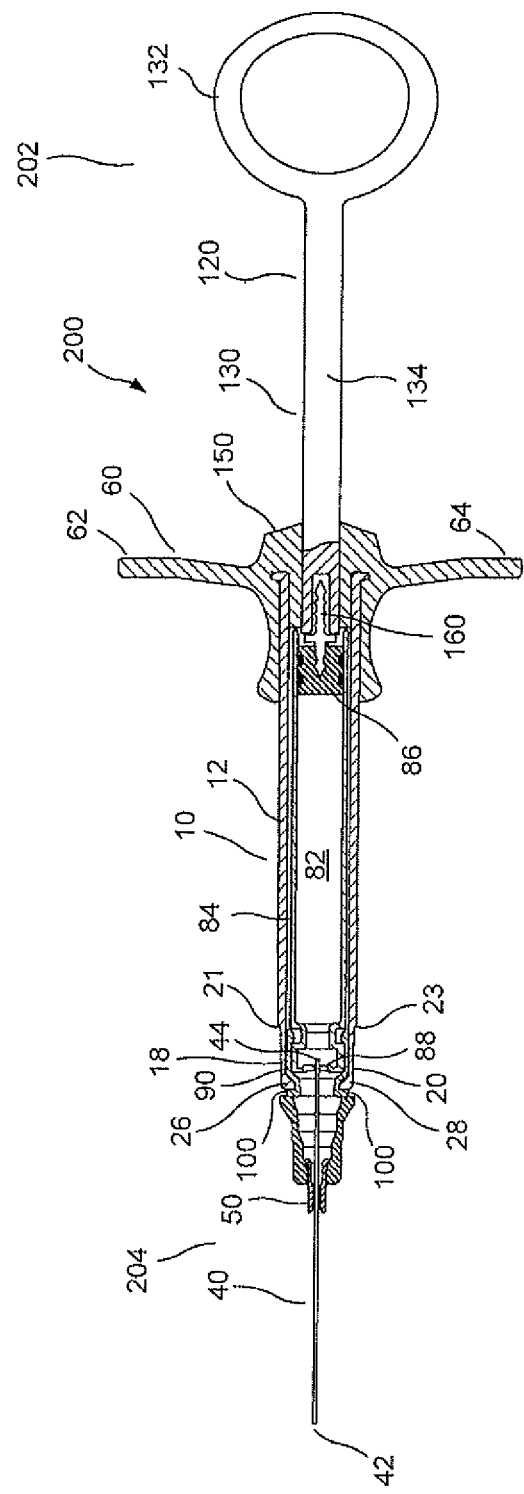
FIG. 18 is a cross-sectional view of an alternative embodiment the assembled injection device of the present disclosure in the armed configuration.

FIGS. 17, 18 and 19 illustrate an alternative embodiment of the injection device 200 of the present disclosure, wherein the housing 12 does not include the mounting hub 12A.

The embodiment of FIGS. 17, 18 and 19 includes some different elements from the other embodiment. For instance, the finger flange assembly 60 includes first and second notches 65, 67 and further includes central bore 66 which with an internal annular snap ring 69 which is snap engaged between the first and second external snap ridges 153, 155 of the plunger cap 150. This forms a sandwiched engagement between the rear annular rim 16 of housing 10 between the finger flange assembly 60 and the plunger cap 150. This sandwiched engagement is sufficiently tight to ensure structural stability but retains the ability of the finger flange assembly 60 to rotate with respect to the housing 10. Furthermore, a snap detent engagement is formed between an annular snap ring ridge 140 on the shaft 134 of plunger rod 130 and an annular snap notch of the plunger cap 150.

In order to arm the injection device 200 for an injection, the user removes the injection device 200 from the flow wrapper package. The user then removes the needle sheath 70 from the housing 10 of injection device 200. The removal of needle sheath 70 from the housing 10 removes the constraint on the outward flexure of first and second cantilevered locking tabs 18, 20. The user then manually engages the finger flanges 62, 64 and the circular thumb ring 132 in the conventional manner and depresses the circular thumb ring 132. This releases, overcomes, or disengages the detent or snap-fit engagement between the annular retention channel shaft 134 of the plunger rod assembly and the annular retention ring 95 of mounting hub 12A (often producing audible feedback) and drives the harpoon 160 into engagement with the cartridge plunger 86 of cartridge 82. Further movement of the plunger rod 30 urges the cartridge 82 and the cartridge-to-housing interface 90 (i.e., the cartridge subassembly 118) forward. It is noted that while the cartridge 82 is sealed with the cap 88 intact, the cartridge plunger 86 cannot move within the cylindrical wall 84 of cartridge 82 and insertion of the plunger rod 30 is translated into forward movement of the cartridge 82 and the cartridge-to-housing interface 90 toward the distal end 204. This forward movement further causes the outward flexure of the first and second cantilevered locking tabs 18, 20 as the second end 98 of cartridge-to-housing interface 90 is urged against the ramped portions 25 of first and second latching bosses 26, 28 of first and second cantilevered locking tabs 18, 20. As second end 98 of cartridge-to-housing interface 90 passes over the first and second latching bosses 26, 28 and abuts against an interior of the frustoconical section 30, the first and second cantilevered locking tabs 18, 20 snap back into place whereby first and second latching bosses 26, 28 are engaged within annular notch 100 of cartridge-to-housing interface 90. Further, outwardly flared edge 99 of second end 98 of cartridge-to-housing interface 90 is engaged between the interior of the frustonical section 30 and the transverse orthogonal wall 29 of first and second latching bosses 26, 28. Additionally, this forward movement of the cartridge 82 causes the butt end 44 of cannula 40 to pierce the septum 89 of cartridge 82 thereby providing a sterile fluid pathway between the cartridge 82 and the cannula 40. Often, audible feedback is generated when the injection device 200 goes from the first engagement or pre-armed position (FIG. 1A) to the second engagement or armed position (FIG. 1B). The audible feedback provides the medical professional with an indication that the needle or cannula 40 is engaged to fully connect the fluid pathway. With the position of the cartridge 82 stabilized by the engagement between the first and second cantilevered latching tabs 18, 20 and the cartridge-to-housing interface 90, and with the septum 89 pierced, further depression or insertion of the plunger rod 130 drives the cartridge plunger 86 further into the cartridge 82 thereby causing the ejection of the injectable agent out of the cartridge 82 through the central passageway 46 of cannula 40 for injection into a patient.

Figure 14:
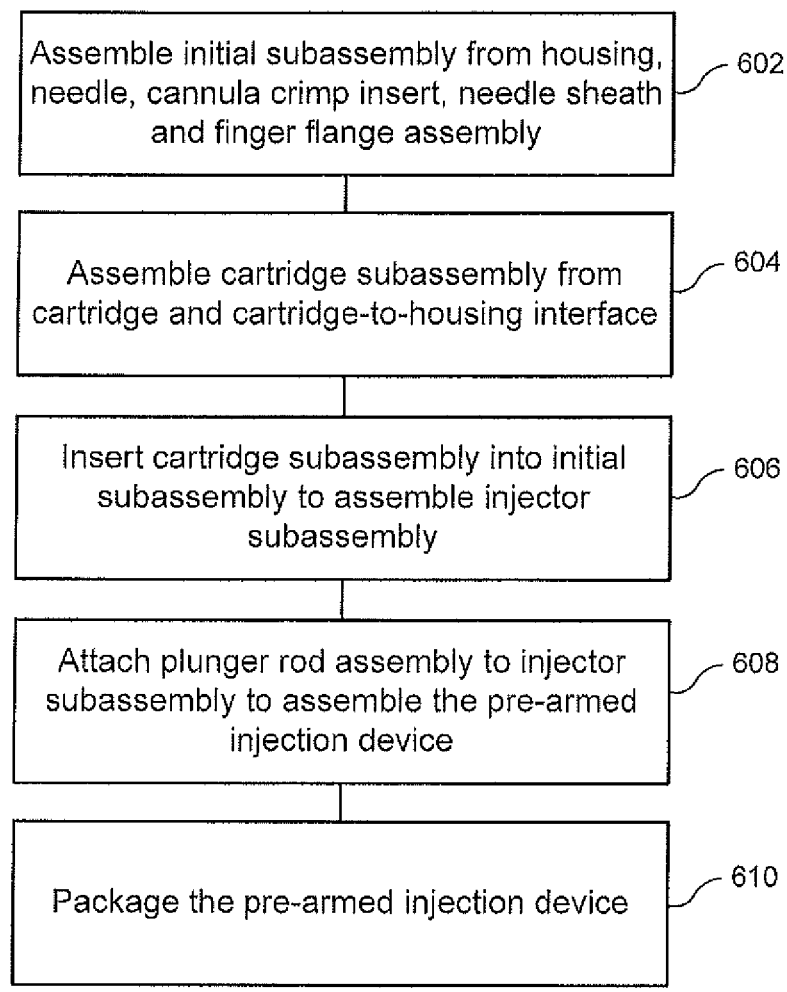
FIG. 14 is a flowchart of the assembly of the injection device of the present disclosure.

FIG. 14 illustrates an exemplary assembly or manufacturing method for injection device 200, but the assembly or manufacture of injection device 200 is not limited thereto. The order of steps presented is merely illustrative and may be performed in a different order or in parallel operations.

In step 602, which is performed in an aseptic environment at least with respect to the needle 40 and any elements which form the sterile fluid pathway, the cannula crimp insert 50, with the needle 40 inserted therein, is inserted into the forward nose 14 of housing 10. Additionally, the needle sheath 70 is mounted on the housing 10 and the finger flange assembly 60 is positioned on the mounting hub 34 of housing 10 thereby resulting in the initial subassembly 80 of FIGS. 3 and 4. In step 604, which is performed in an aseptic environment at least with respect to the septum 89 and the cartridge-to housing interface 90 to the extent that they form the sterile fluid pathway, the cartridge 82 is inserted into the cartridge-to-housing interface 90 thereby resulting in the cartridge subassembly 118 of FIGS. 5 and 6. In step 606, which is performed in an aseptic environment, the cartridge subassembly 118 of FIGS. 5 and 6 is inserted into the initial subassembly 80 of FIGS. 3 and 4 thereby resulting in the injector subassembly 119 of FIGS. 7A, 7B and 7C. In step 608, which is not necessarily performed in an aseptic environment, the plunger rod assembly 120 is attached to the injector subassembly 119 as shown in FIGS. 10A, 10B and 10C thereby resulting in the pre-armed injection device 200 of FIG. 10C as well as FIG. 1A. In step 610, the resulting injection device 200 may be packaged, which is not necessarily performed in an aseptic environment.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. An injection device comprising:
   a cartridge with a first cartridge end and a second cartridge end, the first cartridge end being closed and the second end including a cartridge plunger, the first cartridge end including a septum and a cap securing the septum to the first cartridge end;
   a housing enclosing the cartridge, the housing including a first housing end and a second housing end, the housing including at least one movable cartridge stop;
   a needle including a cannula, the needle being engaged to the first end of the housing; and
   a cartridge adapter separately formed from the cap and the cartridge and having a first adapter end and a second adapter end, the first adapter end receiving and engaging the cap at the first cartridge end, the adapter further including an annular element slidably engageable within the movable cartridge stop, wherein the adapter is movable between a first position and a second position with respect to the at least one movable cartridge stop, wherein the annular element is disposed distally of the cartridge.

2. The injection device of claim 1 wherein in the first position, the cannula is spaced away from the first cartridge end and wherein in the second position, the cannula penetrates the first cartridge end thereby providing communication of contents of the cartridge to the cannula.

3. The injection device of claim 2 wherein in the first position, the cartridge adapter abuts the at least one movable cartridge stop thereby maintaining a position of the cartridge and maintaining separation between the cannula and the first cartridge end, and wherein in the second position, the annular element is in detent engagement with the movable cartridge stop.

4. The injection device of claim 3 wherein in the first position, the annular element is free of engagement with the at least one movable cartridge stop.

5. The injection device of claim 3 wherein annular element is an annular notch disposed distal of the cap.

6. The injection device of claim 5 wherein the at least one movable cartridge stop includes at least one cantilevered tab.

7. The injection device of claim 6 wherein the housing further includes at least one wall and the at least one cantilevered tab is formed from the at least one wall.

8. The injection device of claim 7 wherein the at least one wall is a cylindrical wall.

9. The injection device of claim 7 further including a sheath covering the needle, the sheath including a first sheath end and a second sheath end, wherein the first sheath end is open and is engageable with the housing so as to prevent outward movement of the at least one cantilevered tab.

10. The injection device of claim 9 wherein when the sheath engages the housing, the cartridge adapter is prevented from moving from the first position to the second position and wherein when the sheath is removed from sheath, the at least one cantilevered tab can flex outward thereby allowing the cartridge adapter to move from the first position to the second position.

11. The injection device of claim 10 further including a plunger rod assembly extending through the second housing end, for engagement with the cartridge plunger.

12. The injection device of claim 11 wherein when the sheath is removed from the housing, movement of the plunger rod assembly can move the cartridge adapter from the first position to the second position.

13. The injection device of claim 12 wherein the plunger rod assembly includes a plunger detent element for engaging the second housing end, thereby holding the plunger rod assembly in place prior to engagement with the cartridge plunger.

14. The injection device of claim 13 wherein the plunger detent element provides a snap detent engagement between the plunger rod and the second housing end, whereby user operation of the plunger rod builds up force prior to release of the snap detent engagement thereby increasing a velocity of the plunger rod.

15. The injection device of claim 13 wherein disengagement of the plunger detent element produces tactile feedback.

16. The injection device of claim 12 further including a radially extending finger flange assembly proximate to the second housing end.

17. The injection device of claim 12 wherein the finger flange assembly is rotatable with respect to the housing.

18. The injection device of claim 1 wherein the cap is made of metal.

19. The injection device of claim 18 wherein the cartridge includes a drug or pharmaceutical product.

20. The injection device of claim 1 wherein an inner surface of the cartridge adapter engages an outer surface of the cap.

21. The injection device of claim 1 wherein the cartridge adapter extends distally from the cap.

22. A method of assembly of an injection device, including the steps of:
providing a housing including a first housing end, a second housing end, at least one wall and at least one housing stop element;
providing a needle including a needle cannula;
engaging the needle within the housing;
providing a needle sheath with a first sheath end and a second sheath end, wherein the first sheath end is open;
engaging the needle sheath to the housing thereby covering at least a part of the cannula and restraining movement of the at least one housing stop element;
providing a finger flange assembly;
attaching the finger flange assembly proximate to the second housing end;
providing an adapter including an annular element;
providing a cartridge including a first cartridge end which is closed and a second cartridge end which includes a cartridge plunger, the first cartridge end including a septum and a cap securing the septum to the first cartridge end;
attaching the first cartridge end of the cartridge to the adapter such that the adapter receives and engages the cap of the cartridge, the adapter being separately formed from the cap and the cartridge;
inserting the cartridge and the adapter into the second housing end whereby the cartridge is in a first position with respect to the at least one housing stop element, wherein the annular element is disposed distally of the cartridge and slidably engageable within the at least one housing stop element;
providing a plunger rod including a shaft and an element for engagement with the cartridge plunger; and
inserting the shaft into the second housing end;
whereby subsequent removal of the needle sheath allows movement of the at least one housing stop element and allows the adapter to move to a second position with respect to the at least one housing stop element.

23. The method of claim 22 wherein in the first position of the adapter with respect to the at least one housing stop element, the needle cannula is separated from the first cartridge end, and wherein the second position of the adapter with respect to the at least one housing stop element, the needle cannula punctures the first cartridge end.

24. The method of claim 23 further including the step of sterilizing the first cartridge end prior to the step of attaching the first cartridge end of the cartridge to the adapter.

25. The method of claim 24 wherein the step of sterilizing the first cartridge end is performed by pulsed ultra-violet light.

26. The method of claim 25 further including the step of sterilizing at least a portion of the adapter prior to the step of attaching the first cartridge end of the cartridge to the adapter.

27. The method of claim 26 wherein the step of sterilizing at least a portion of the adapter is performed by bulk gamma ray or ultra-violet sterilization.

28. The method of claim 22 wherein the cartridge contains a drug or pharmaceutical product.

29. An injection device comprising:
a cartridge with a first cartridge end and a second cartridge end, the first cartridge end being closed and the second end including a cartridge plunger, the first cartridge end including a cap;
a housing enclosing the cartridge, the housing including a first housing end and a second housing end, the housing including at least one movable cartridge stop;
a needle including a cannula, the needle being engaged to the first end of the housing; and
a cartridge adapter with a first adapter end and a second adapter end, an inner surface of the cartridge adapter at the first adapter end engaging an outer surface of the cap, the adapter further including an annular element slidably engageable within the movable cartridge stop, wherein the adapter is movable between a first position and a second position with respect to the at least one movable cartridge stop, wherein the annular element is disposed distally of the cartridge; and a plunger rod assembly extending through the second housing end, for engagement with the cartridge plunger.

30. The injection device of claim 29 further including a sheath covering the needle, the sheath including a first sheath end and a second sheath end, wherein the first sheath end is open and is engageable with the housing so as to prevent outward movement of the at least one movable cartridge stop.

31. The injection device of claim 30 wherein when the sheath engages the housing, the cartridge adapter is prevented from moving from the first position to the second position and wherein when the sheath is removed from sheath, the at least one movable cartridge stop can flex outward thereby allowing the cartridge adapter to move from the first position to the second position.

* * * * *